United States Patent [19]

Neas et al.

[11] Patent Number: 4,861,556
[45] Date of Patent: Aug. 29, 1989

[54] MICROWAVE-BASED APPARATUS AND KJELDAHL METHOD

[75] Inventors: Edwin D. Neas, Indian Trail, N.C.; Terry S. Floyd, Clover, S.C.

[73] Assignee: CEM Corporation, Matthews, N.C.

[21] Appl. No.: 55,921

[22] Filed: Jun. 8, 1987

Related U.S. Application Data

[63] Continuation-in-part of Ser. No. 874,278, Jun. 13, 1986, abandoned.

[51] Int. Cl.⁴ ............................................. G01N 31/12
[52] U.S. Cl. ....................................... 422/78; 422/80; 436/175; 219/10.55 R; 219/10.55 A
[58] Field of Search ................... 422/68, 78, 79, 80, 422/102; 436/175; 219/10.55 R, 10.55 A

[56] References Cited

U.S. PATENT DOCUMENTS

| | | | |
|---|---|---|---|
| 2,932,558 | 4/1960 | Bennet | 23/230 |
| 3,437,211 | 4/1969 | Lindsey | 210/406 |
| 3,645,746 | 2/1987 | Hach | 436/115 |
| 3,726,646 | 4/1973 | Kravetz et al. | 436/175 |
| 3,963,420 | 6/1976 | Matsumoto et al. | 23/230 R |
| 4,080,168 | 3/1978 | Abu-Samra et al. | 436/175 |
| 4,307,277 | 12/1981 | Maeda et al. | 219/10.55 R |
| 4,347,216 | 8/1982 | Kawasaki et al. | 422/78 |
| 4,363,639 | 12/1982 | Gladon | 55/95 |
| 4,490,287 | 12/1984 | Hardwick et al. | 252/629 |
| 4,645,745 | 2/1987 | Hach | 436/114 |
| 4,749,245 | 7/1973 | Kerecz | 436/175 |

FOREIGN PATENT DOCUMENTS 1045341 11/1953 France .
1385483 2/1975 United Kingdom .

OTHER PUBLICATIONS

P. Barrett et al, *Analytical Chemistry*, 7, 1021 (1978).
Prolabo literature, for Microwave Digester.
Bradstreet, *The Kjeldahl Method for Organic Nitrogen*, 1965, pp. 40–42.
Kjel-Foss Automatic literature, by A/S N. Foss Electric.
S. Brayton of the Hach Company, "A Practical Kjeldahl-Nitrogen Method".
Heat Systems–Ultrasonics, Inc. literature, for Mystaire ® Laboratory Scrubbers.
Alliger, *American Laboratory*, Dec. 1976.

*Primary Examiner*—Barry S. Richman
*Assistant Examiner*—T. J. Wallen
*Attorney, Agent, or Firm*—Timothy R. Kroboth

[57] ABSTRACT

A microwave-based apparatus useful for rapid digestion is provided. The apparatus includes a hollow tubular body having an end sealingly joined to a reaction vessel disposed within a microwave system. The end of the tubular body has grooves for the flow of air through the sealed tubular body/reaction vessel joint. A scrubber removes digestion off gases. Also provided is a rapid, microwave-based, Kjeldahl digestion method.

14 Claims, 4 Drawing Sheets

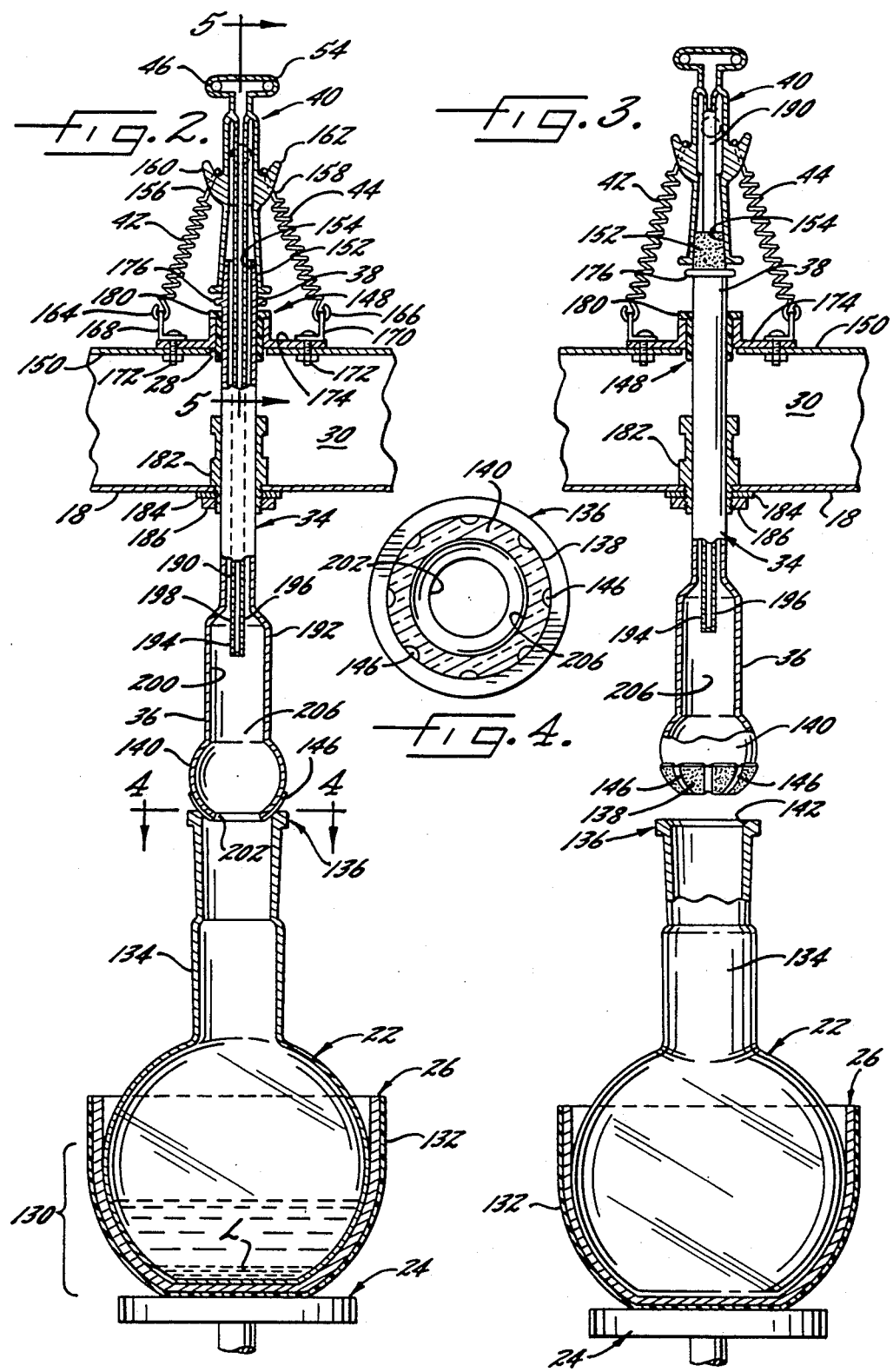

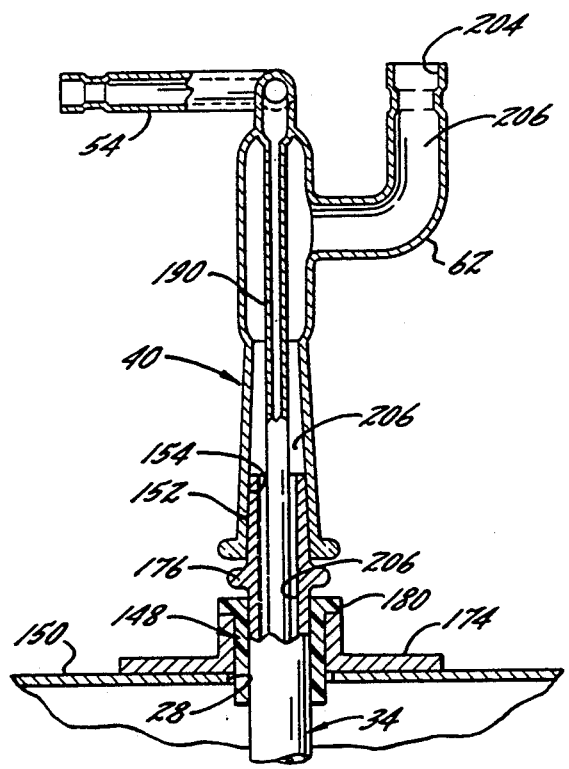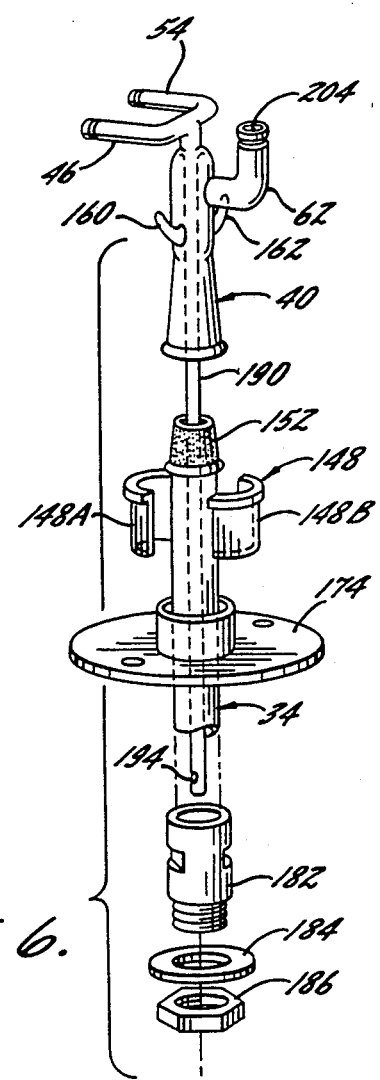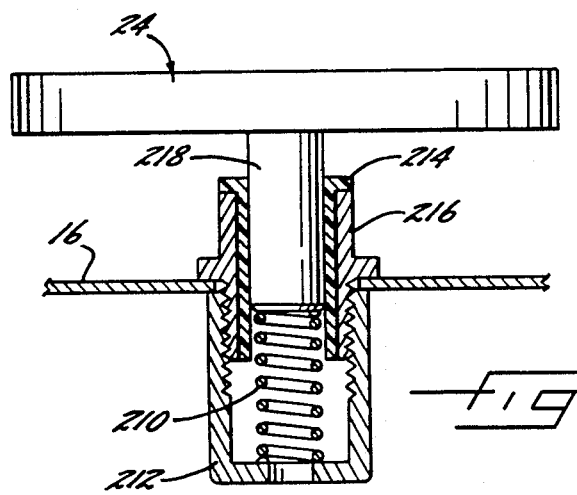

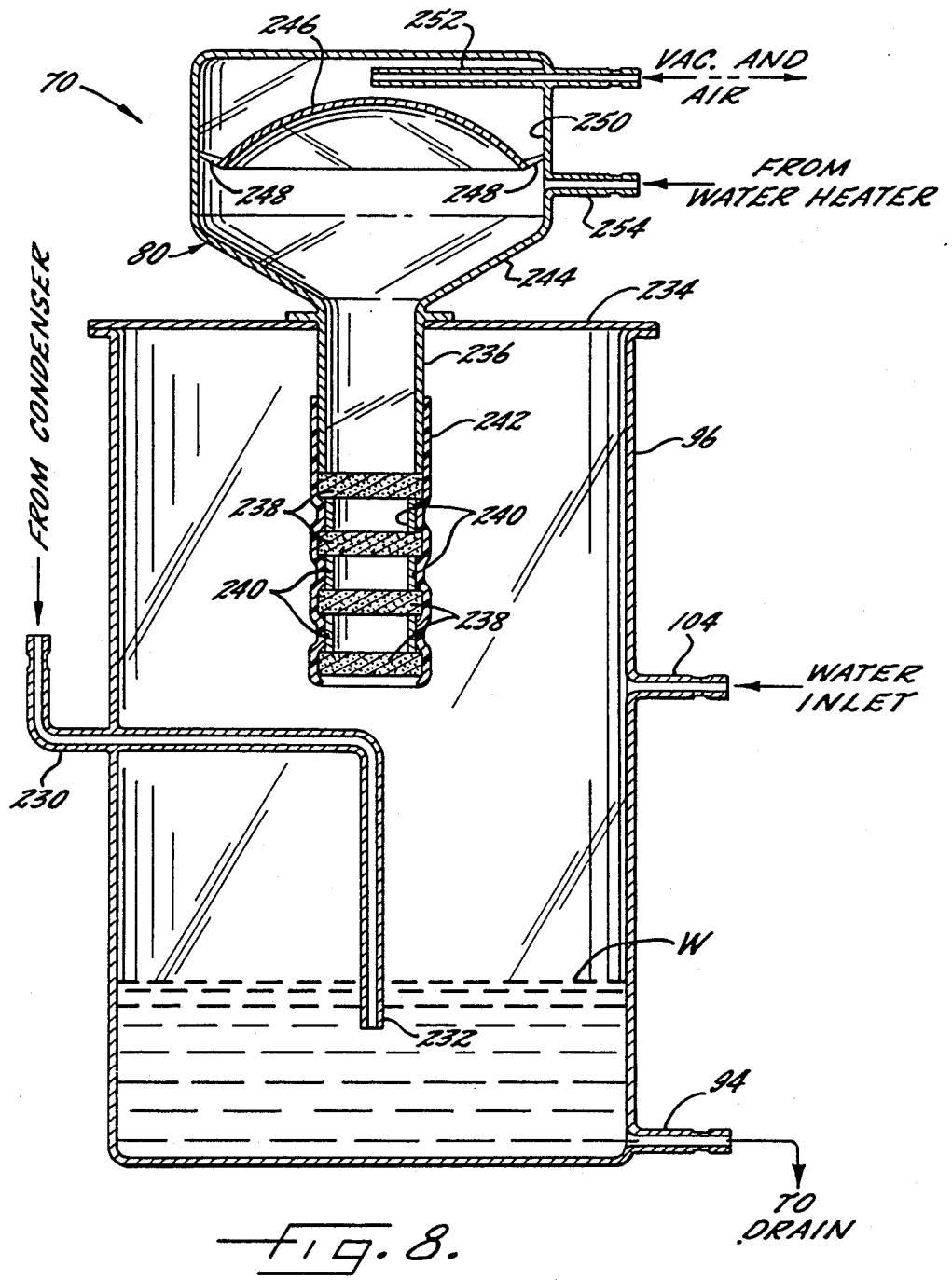

MICROWAVE-BASED APPARATUS AND KJELDAHL METHOD

REFERENCE TO RELATED APPLICATION

This application is a continuation-in-part of patent application Ser. No. 874,278, filed on June 13, 1986, now abandoned.

TECHNICAL FIELD

The present invention relates to a microwave-based apparatus useful for rapid digestion, and to a rapid, microwave-based, Kjeldahl digestion method.

BACKGROUND ART

A problem with wet digestion of organic samples, particularly a gas-generating, tissue digestion such as the Kjeldahl digestion, is boil-over with resultant loss of sample, due to excessive foaming and/or bumping. Further problems are safe disposal of off gases including the corrosive fumes of an acid digesting agent, loss of acid values during digestion, and, for a Kjeldahl digestion especially, length of digestion time.

In recent years, as illustrated by U.S. Pat. No. 4,080,168 to Abu-Samra et al, U.S. Pat. No. 4,347,216 to Kawasaki et al, P. Barrett et al., *Analytical Chemistry*, 7, 1021 (1978), and a microwave digester made by Prolabo, interest has focused on microwave oven-based wet digestion. However, the problems of small sample size, boil-over, safe disposal of off gases, and loss of acid values exist.

For instance, Abu-Samra et al, while stating that bumping and frothing are virtually eliminated, advise that it may be desirable to incorporate an interrupted duty cycle type of timer to prevent sample boil-over. Kawasaki et al remove off gases through a hollow gas collector connected to an external scrubber and removably mounted, sample decomposing containers; and include an exhaust fan in the microwave oven thereof. However, Kawasaki et al describe a complex equation for selecting an irradiation time and an irradiation interruption period, to control foaming and bumping at an early stage of digestion.

Noting several shortcomings of Abu-Samra et al's fume removal apparatus including deterioration of the interior Plexiglas box, Barrett et al describe a round bottom flask with a ground glass joint connected directly to an exit port which is coupled to an aspirator. However, a ground glass joint in the proximity of a hot, bubbling liquid that may leak into the joint, has a tendency to freeze.

Prolabo's microwave digester vents gases through a container lid connected to a scrubber via a side arm.

As illustrated by R.B. Bradstreet, *The Kjeldahl Method for Organic Nitrogen*, Academic Press, New York, 1965, pp. 40-42, and a Kjeldahl technique of A/S N Foss Electric, hydrogen peroxide is useful as an additive for reducing boil-over. In the Foss Kjeldahl method, a protein sample is mixed with conventional Kjeldahl digestion ingredients, viz., 10-15 ml concentrated sulfuric acid, 0.75 g mercuric oxide catalyst and 15 g potassium sulfate; 10 ml hydrogen peroxide (35%) is combined with the mixture; the mixture is heated using a high flame; the mixture is heated with a low flame; and 110 ml deionized water is added to the digestate, while cooling the reaction vessel using a blower. Although fast compared to other Kjeldahl methods, this method nevertheless requires twelve minutes to produce a digested sample. The method uses a 0.5 sample when protein content is more than 45%, and a 1.0 g sample when protein content is less than 45%. The apparatus used in the method includes a scrubber connected to a side tube of the reaction vessel.

Also known, as exemplified by a publication authored by S. Brayton of the Hach Company and entitled "A Practical Kjeldahl-Nitrogen Method", is a sulfuric acid-stabilized, hydrogen peroxide prepared by mixing 1 part of concentrated sulfuric acid with 4 parts of 50% hydrogen peroxide. As illustrated by U.S. Pat. No. 3,437,211 to Lindsey and U.S. Pat. No. 4,363,639 to Gladon, a connector tube having coaxial inlet/outlet passageways is known, and as exemplified by U.S. Pat. No. 3,963,420 to Matsumoto et al, sample-dissolving apparatus including a condenser, is known.

Considering the foregoing, it can be understood that there is a need for an improved microwave-based apparatus. Furthermore, there is a need for an improved rapid, microwave-based, macro-Kjeldahl digestion method.

DISCLOSURE OF THE INVENTION

It is accordingly an object of the present invention to provide an improved microwave-based apparatus.

It is a further object of the present invention to provide an improved rapid, microwave-based, macro-Kjeldahl digestion method.

Additional objects, advantages and novel features of the present invention are set forth in the description that follows, and in part will become apparent to those skilled in the art upon examination of the following description or may be learned by practice of the invention.

To achieve the foregoing objects and in accordance with the purpose of the present invention, as embodied and broadly described herein, there is provided a microwave-based apparatus useful for a rapid digestion. The apparatus includes a microwave system having a wall with an aperture formed therethrough. Located within a chamber of the microwave system is a reaction vessel. Extending through the wall opening is a hollow tubular body that has an end sealingly mated to the reaction vessel. The apparatus further includes grooves for the flow of air into the hollow tubular body from the microwave chamber. A vacuum pump is in fluid communication with the grooves.

Also provided is an apparatus useful for a rapid digestion that includes a microwave system and a self-contained, scrubber system. Disposed within the microwave system is a reaction vessel, with which the scrubber system is in fluid communication. The scrubber system includes (a) a scrubber tower that includes several scrubber discs spaced apart from one another, and (b) a vacuum pump.

Also provided by the present invention is a rapid, microwave-based, Kjeldahl digestion method. In the method, sufficient microwave energy is applied to an acid/sample mixture to attain an optimum Kjeldahl digestion temperature. The sample has a size of at least about 0.5 g. Sufficient microwave energy is applied until a digestate is formed. After discontinuing the application of microwave energy, the digestate is diluted with water. In the method, the digestion and dilution steps are carried out while removing digestion off gases, and are carried out within a microwave system.

Furthermore, there is provided another rapid, microwave-based, Kjeldahl digestion method. In this method, sufficient microwave energy is applied to an acid/sample mixture to provide an optimum Kjeldahl digestion temperature. Simultaneously, suction is applied to the acid/sample mixture, while controllably inletting ambient air proximate to the locus of digestion off-gas generation. As a result, suction efficiency is increased.

BRIEF DESCRIPTION OF THE DRAWING

Reference is now made to the accompanying drawing, which forms a part of the specification of the present invention, and which depicts a preferred microwave-based apparatus in accordance with the present invention.

FIG. 2 is an enlarged section taken substantially along the line 2—2 of FIG. 1;

FIG. 3 is a view similar to FIG. 2, with connector tube 34 depicted as upwardly displaced;

FIG. 4 is an enlarged section taken substantially along the line 4—4 in FIG. 2;

FIG. 5 is an enlarged section taken along the line 5—5 in FIG. 2;

FIG. 6 is an exploded, perspective view of a portion of the apparatus of FIG. 1;

FIG. 7 is an enlarged view taken substantially along line 7—7 in FIG. 1; and

FIG. 8 is an enlarged sectional view of the scrubber unit shown in FIG. 1.

BEST MODE FOR CARRYING OUT THE INVENTION

Figure 1:
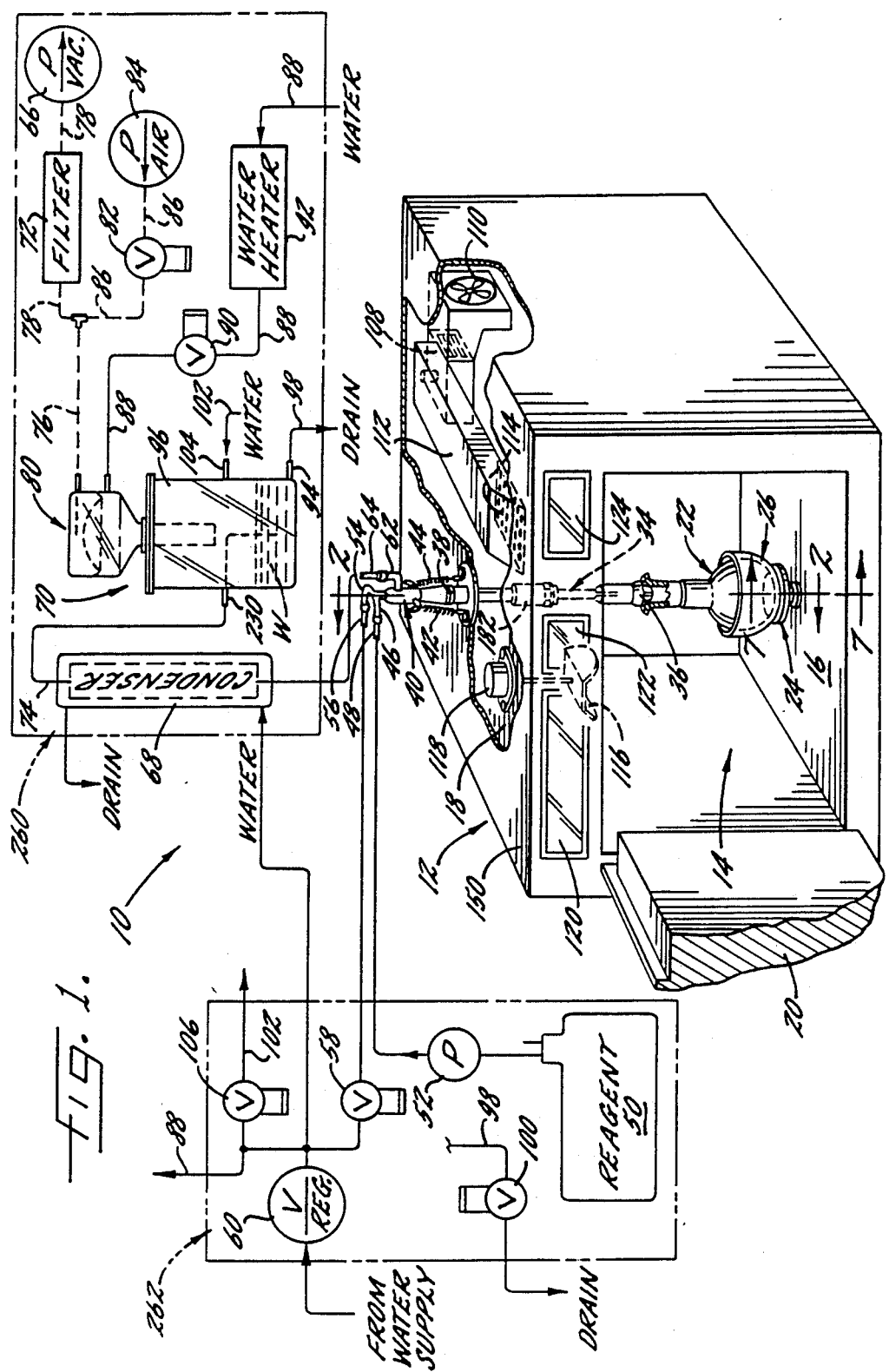
FIG. 1 is a schematic view of a preferred microwave-based apparatus in accordance with the present invention, which includes a microwave system 12, portions of which are broken away, a self-contained scrubber system 260, and a compact fluid-delivery system 262.

As explained earlier, the present invention is directed to a microwave-based apparatus useful for rapid digestion, and to a rapid Kjeldahl digestion method using the apparatus. An important feature of the invention is that it is useful for macro-Kjeldahl digestions, that is, the digestion of a sample weighing about 0.5–1.0 g or more.

In the following description, certain terms such as "upper", "lower", "above", "upward", "downward", "upwardly" and "downwardly", are intended to designate relative orientation as shown in the drawing.

FIG. 1 depicts a preferred microwave-based, apparatus 10 in accordance with the present invention. As the description of the apparatus proceeds, it will become plain that the apparatus need not include certain of the described features when the apparatus is used for purposes other than Kjeldahl digestions.

Apparatus 10 includes a microwave system 12 with an internal chamber 14 formed in part by a floor 16, a chamber ceiling 18, shown in FIG. 2, and a door 20. Suitably, the chamber is stainless steel. Within chamber 14 is a reaction vessel 22, which is preferably disposed on a spring-loaded platform 24 and insulated by a cup 26.

It is preferred for reaction vessel 22 to be a flat bottom, boiling flask. A particularly suitable material for the reaction vessel is borosilicate or quartz glass, with quartz glass being preferred. Compared to a borosilicate glass vessel, a quartz vessel is more microwave transparent, thereby providing a relatively shorter digestion time, the power output being constant. Furthermore, a quartz vessel withstands thermal shock better than a borosilicate glass vessel. Moreover, for a sample containing more than about 30% protein, especially 45% or more protein, a quartz vessel has been surprisingly found to yield more accurate results.

Referring also to FIG. 2, extending through an aperture 28 of a top wall 30 of microwave system 12 is a connector tube 34, which has a lower end 36 joined to reaction vessel 22. Protruding above top wall 30 is an upper end 38 of the connector tube, which is joined to an input/output tree 40. Springs 42,44 bias lower end 36 of the connector tube to form a tight seal with reaction vessel 22.

With reference to FIG. 1, attached to an input tube 46 of tree 40 is a section 48 of tubing that connects input tube 46 to a reagent reservoir 50 through a pump 52, which is advantageously a peristaltic pump. Preferably, for a Kjeldahl digestion, reservoir 50 contains a mixture of concentrated sulfuric acid and hydrogen peroxide.

Connecting an input tube 54 of tree 40 to, in the case of a Kjeldahl digestion, a water supply, is a section 56 of tubing. Delivery of water to input tube 54 and water pressure regulation are provided by a solenoid valve 58 and a pressure regulator 60, respectively.

Attached to an output/input tube 62 of tree 40 is a section 64 of tubing that connects tube 62 to a vacuum pump 62 through a water-cooled condenser 68, a scrubber unit 70 and a filter 72. Pump 62 is suitably a diaphragm-type pump. For Kjeldahl digestions, filter 72 is advantageously an activated carbon filter. Connecting the condenser to the scrubber unit is line 74, and connecting the scrubber unit to the vacuum pump are lines 76,78.

Water for cooling the condenser is passed from a water supply through pressure regulator 60 to provide a controlled flow of cooling water. Condensate from the condenser returns by gravity to reaction vessel 22 through tubing section 64 and output/input tube 62.

Connected to a scrubber tower 80 of the scrubber unit via a solenoid valve 82, is an air pump 84. Lines 76,86 provide the connection, with line 76 conveniently providing a common connection to the scrubber tower for the vacuum pump and the air pump. The air pump provides a pressurized air flow for flushing the scrubber tower.

A hot water line 88 connects the water supply to the scrubber tower through a solenoid valve 90, a heater 92, and pressure regulator 60. This line provides the delivery of hot water, for backflushing the scrubber tower.

Connected to a drain port 94 of a collector 96 of the scrubber unit is a drain line 98, which is regulated by a solenoid valve 100. Solenoid valve 100 opens drain line 98 during backflushing, to drain the contents from the collector.

A fill water line 102 connects an inlet port 104 of collector 96 to the water supply through a solenoid valve 106 and pressure regulator 60. Fill water line 102 delivers a predetermined volume of water, designated W, to the collector after draining through drain line 98 is complete.

Microwave system 12 includes a magnetron 108, a fan 110 for cooling the magnetron, a wave guide 112, and a waveguide opening 114. Microwaves pass into interior chamber 14 of the microwave system through opening 114. Located within chamber 14 is a mode stirrer 116, which is operated by a motor 118.

Panels 120,122,124 provide for computer control of peristaltic pump 52, solenoid valves 58,82,90,100,106, and vacuum pump 66, and for information display. For instance, under computer control, a predetermined volume of a liquid reagent may be delivered from reservoir 50 to reaction vessel 22 at a desired time; a predetermined volume of another fluid may be delivered to the reaction vessel at a desired time, either continuously or in pulses; the vacuum pump may be turned off and the air pump turned on at a desired time; and a predetermined volume of hot water may be delivered to the scrubber tower at a desired time.

With reference to FIG. 2, a lower portion 130 of the rounded part of reaction vessel 22 is insulated by cup 26. It is intended that the contents level within the vessel during the application of microwave energy, be within lower portion 130.

The insulator cup advantageously includes a protective outer liner 132. Liner 132, which is suitably made of a plastic, increases the durability of cup 26 and facilitates the insertion and removal of reaction vessel 22.

Cup 26 has a shape that conforms to the contour of lower portion 130. The cup is made of a microwave-transparent insulator that is preferably a moldable material capable of withstanding temperatures up to about 500° C., such as glass fiber.

When a glass fiber cup is used, an upper region of the cup may be hand molded to conform to the vessel contour after the reaction vessel has been inserted into the cup, to provide further insulation. A suitable glass fiber cup has a thickness of about 4.5 mm+/−1 mm.

Referring to FIG. 3, reaction vessel 22 has a neck 134 that terminates in an inwardly tapered mouth 136. The angle of inward taper provides for mouth 136 to sealingly mate with a surface 138 of a generally rounded joint 140 of lower end 36 of the connector tube. Preferably, the angle of taper is about 45°. Advantageously, neck 134 ends in the inwardly ground mouth of a 29/42 ground glass joint.

Providing the inward taper to mouth 136 is a narrow, circumferential, inner wall 142 having a radius of approximately 3/32″. This radius provides a contact area that is sufficient to form a tight seal between the connector tube and reaction vessel, but yet that prevents freeze-up of the connector tube/reaction vessel juncture.

Lower end 36 of the connector tube is advantageously bell-shaped, and surface 138 of rounded joint 140 is preferably of ground glass. The rounded shape of joint 142 assists an operator in connecting the reaction vessel to the downwardly-biased connector tube.

With reference also to FIG. 4, cut through surface 138 and into joint 140 are grooves 146, which provide inward air flow through the connector tube/reaction vessel juncture. The locus of inward air flow provided by the grooves, is suitably proximate to the mouth of the reaction vessel. Air is drawn from internal chamber 14 through these grooves into the connector tube, by vacuum pump 66.

Each groove is oriented so as to break the air-tight seal provided by surface 138 and inner wall 142 of the reaction vessel mouth. Therefore, the grooves are suitably oriented longitudinally, that is, parallel to the longitudinal axis of the connector tube.

Preferably, the grooves maximize the flow of air drawn by the vacuum pump from internal chamber 14, and provide a high velocity of air flow through the reaction vessel mouth. We have found that several smaller grooves work better than a few larger grooves that would provide the same volume of air flow, as the larger grooves would produce a relatively lower velocity of air flow.

Suitably, eight grooves equally distributed around the circumference of ball joint 140, may be used, with the area of a groove opening being 0.0015 sq.in. This area provides a flow rate per groove of 0.068 cfm, and a total flow rate of 0.544 cfm.

As can be understood, the grooves cooperate with the vacuum pump to draw off gases and entrained solids out of the reaction vessel. In so doing, the grooves prevent escape of fumes into chamber 14 and even pressure build-up that could otherwise cause a mechanical bumping in which the connector tube/reaction vessel joint momentarily opens and closes as off gases escape through the joint.

Furthermore, air flow provided by the grooves cools the connector tube/reaction vessel juncture, the connector tube, and tree 40. As a result, tubing connecting to tree 40, lasts longer.

Referring again to FIG. 2, connector tube 34 extends through aperture 28 of top wall 30. Aperture 28 advantageously has a diameter of about one-half inch. A split bushing 148, suitably made of a heat-resistant material such as Teflon ®, effects a snug fit between the connector tube and an exterior panel 150 of the top wall. As shown in FIG. 6, bushing 148 splits into two pieces 148A and 148B for assembly.

Exterior to the top wall is a male joint 152 of upper end 38 of the connector tube. Male joint 152 forms an air-tight friction seal with a female joint 154 of input-/output tree 40. Preferably, connector tube 34 and tree 40 are made of glass, and joints 152,154 are tapered, ground glass joints.

Upper spring ends 156,158 are attached to tree arms 160,162, respectively, and lower spring ends 164,166 attach to spring anchor clips 168,170, respectively. Screws 172 anchor the clips and a mounting bracket 174 to exterior panel 150. Mounting bracket 174 holds split bushing 148 in place.

As shown best in FIG. 5, a connector tube shoulder 176 located below male joint 152, seats on a flange 180 of bushing 148 to limit the downwardly biased movement of the connector tube. Spring biasing of the connector tube makes forming and maintaining a tight seal between the connector tube and reaction vessel easy. Furthermore, the spring biasing facilitates breaking the seal and vessel removal. FIG. 3 depicts an upwardly displaced connector tube.

With reference again to FIG. 2, RF stub 182 provides a radiation-tight seal between connector tube 34 and chamber ceiling 18. Stub 182 is secured to ceiling 18 by a washer 184 and a nut 186.

Referring particularly to FIG. 6, input tubes 46,54 of tree 40 combine to form an inlet tube 190 that extends through connector tube 34. Inlet tube 190 is coaxially disposed within the connector tube.

With reference again to FIG. 2, inlet tube 190 terminates in an upper part 192 of bell-shaped, lower end 36 of the connector tube. An aperture 194 in a delivery end 196 of the inlet tube is disposed in an inlet tube side wall 198 so as to direct fluid flow against an inner wall surface 200 of lower end 36. Alternatively, inlet tube 190 could have an open lower end.

Extending from an opening 202 in rounded joint 140 of the connector tube to a mouth 204 (shown in FIG. 5) of output/input tube 62 is a passageway 206, through which off gases and entrained solids escape from the reaction vessel.

Referring to FIG. 7, platform 24 is biased upwardly by a spring 210 disposed in a cup 212 situated beneath floor 16 of the internal chamber of the microwave system. A bushing 214 and an RF stub 216 effect a snug fit between a leg 218 of the platform and floor 16. Stub 216 is threaded into cup 212, thereby securing both stub 216 and the cup. The stub provides a radiation-tight seal. As spring 210 is located outside chamber 14, the spring may be metallic.

Spring biasing of the platform and of the connector tube make it easy to form and maintain a tight seal between the connector tube and reaction vessel. Furthermore, the spring biasing facilitates breaking the seal and vessel removal.

With reference to FIG. 8, scrubber tower 80 and collector 96 form scrubber unit 70. An inlet tube 230, which communicates with the condenser, has an end 232 disposed below the surface of water W to provide a water trap. The condenser begins the process of cooling the off gases, and the scrubber unit completes the cooling process and removes noxious off gas fumes and entrained solids.

Extending into the collector through a lid 234 is a neck portion 236 of the scrubber tower. Disposed within the neck portion are scrubber discs 238 spaced apart by spacers 240, suitably made of polyvinyl chloride plastic. Snugly surrounding the discs and spacers is a flexible sleeve 242, suitably made of silicone rubber.

Advantageously, the scrubber discs are a sintered glass material. As can be appreciated, an appropriate pore size and number of discs needed, depend upon an intended use, for instance, the gases and/or solids one desires to remove. For Kjeldahl digestions, we have found that two coarse discs as lower discs, and two fine discs as upper discs are quite effective.

For Kjeldahl digestions, a preferred coarse disc has pore size of about 250-500 microns, and is manufactured by Schott; and a preferred fine disc has a pore size of about 40-60 microns, and is manufactured by Corning. Suitably, the discs have a diameter of about 1¼" and a thickness of about ¼".

Typically, one would desire to scrub off gas as rapidly as it is generated. However, we have found that it is beneficial for the scrubber discs to have a pore size that restricts the flow of off gas such that off gas builds up and is contained within collector 96, which functions as a residence reservoir for unscrubbed off gas. Suitably for Kjedahl digestions, collector 96 has volume of 4 to 5 liters.

Situated outside the collector is a chamber portion 244 of the scrubber tower, which includes a dome-shaped splash shield 246. Shield 246 is attached by three legs 248, only two of which are shown, to an inner wall 250 of chamber portion 244. Shield 246 is located between the scrubber discs and tube 252, which communicates with filter 72, so as to prevent condensate from splashing over to the filter. Situated below shield 246 is a hot water inlet port 254.

Use of microwave-based apparatus 10 in a unique macro-Kjeldahl digestion method is now described. The amounts of the various ingredients and the particular time periods described, are appropriate for a 0.5 g protein sample containing 45% or more protein. Twice as large a protein sample would be used when the sample includes less than 45% protein.

A protein sample, preferably either a 0.5 g or 1.0 g sample depending upon the % protein, is added to reaction vessel 22, with conventional Kjeldahl digestion ingredients, to wit, about 10-15 ml of concentrated sulfuric acid, about 0.75 g of mercuric oxide, and about 15 g of potassium sulfate, to provide vessel contents L, depicted in FIG. 2.

The insulated vessel is placed on the platform in the internal chamber of microwave system 12, which has a power output of about 700-1000 watts, a tight seal is formed between the vessel and the connector tube, the microwave door is closed, and the vacuum pump is turned on.

Preferably, a boil-over reducing additive, such as aqueous hydrogen peroxide solution, is added to the reaction vessel. Control is provided by peristaltic pump 52. The additive is passed through input tube 46 of tree 40 and inlet tube 190 into the reaction vessel.

Advantageously, about 12 ml of an about 50% hydrogen peroxide solution may be added in three portions, with a portion being rapidly added at the beginning of the digestion, after about 20-40 seconds, and after about 50-70 seconds. Alternatively, a slow, continuous addition of the hydrogen peroxide solution may be employed. Regardless of whether an intermittent or continuous addition is used, the additive is used in an amount sufficient to reduce boilover. Hydrogen peroxide may assist rapid digestion.

A highly preferred hydrogen peroxide solution is sulfuric acid-stabilized, and is prepared by mixing about 1 part of concentrated sulfuric acid with about 4-8 parts of 50% hydrogen peroxide. When a sulfuric acid-stabilized, hydrogen peroxide solution is used for adding peroxide, sulfuric acid is also thereby added. As a consequence, less sulfuric acid is initially added to the reaction vessel.

As the first portion of boil-over reducing additive is introduced into vessel 22, digestion may be begun by the application of microwave energy to the vessel contents. In a first stage of the digestion step, the vessel contents are heated to quickly attain a digestion temperature generally ranging from about 325° to 350° C. Gas generation with resultant foaming and/or bumping, characterizes this heating stage. Overshooting the optimum temperature results in an erroneously lower protein number.

Typically, the digestion temperature is quickly reached by using a 100% power output for approximately 1-2 minutes. By comparison, if the insulator cup were absent, minutes would be added to this stage of the digestion step due to heat loss through the reaction vessel walls. Furthermore, without the insulator cup, the number of samples that can be simultaneously digested would be power limited.

In a second heating stage, the power output is adjusted to provide an optimum digestion temperature of about 375°-425° C., until digestion is complete. This stage is typically accomplished by heating the vessel contents using about 70% power for about 2-4 minutes.

It will be understood that the connector tube and condenser 68 function to reduce acid loss. Moreover, selection of a 500 ml size for the reaction vessel reduces the loss of acid.

After the digestion step is completed and the application of microwave energy is discontinued, a dilution step may be immediately commenced. In this step, water is injected into the reaction vessel through input tube 54 of tree 40 and inlet tube 190. Mixing of the water with the hot digestate results in the evolution of a large volume of gas. The volume of water to be added is catalyst dependent, with about 140-150 ml of water being suitable in the case of a mercuric oxide catalyst.

For a mercuric oxide catalyst, about 140-150 ml of water, about 12 ml of peroxide, and about 13 ml of concentrated sulfuric acid represent minimum volumes, and as such are preferred, particularly since a relatively greater liquid volume in the digestion step results in a relatively longer time to reach the optimum temperature, the power output being constant.

To be able to immediately begin the dilution step, that is, to avoid an intervening cooling step, a pulsed addition of water is preferably employed, followed by continuous water addition. Pulsed addition is provided by solenoid valve 58.

A preferred pulsing technique involves intermittently opening and closing the water input line for about 40-70 seconds. For each pulse, the water line is suitably open for about 0.1-0.3 seconds and closed for about 1-4 seconds.

The remaining volume of water is thereafter continuously added for about 20-80 seconds.

If a pulsed addition will not be used at the beginning of the dilution step, a cooling step should be employed to prevent a sudden surge in gas evolution. The cooldown period may be several minutes or longer. The overall time will be substantially increased.

Opening 194 in inlet tube 190 directs a fluid against connector tube inner wall surface 200, and the fluid flows down the inner wall into vessel 22. As a result, water is pre-heated prior to reaching vessel 22. Preheating may further control gas evolution.

During the digestion and dilution steps, vacuum pump 66 draws reaction off gases and entrained fat particles from the reaction vessel, through passageway 206 and output/input tube 62 of tree 40, and into water-cooled condenser 68. Grooves 146 enable the vacuum pump to effectively accomplish this so that a large pressure build-up within the reaction vessel and/or connector tube is prevented.

In the condenser, off gas condensate is formed. Condensation provided by water cooling, permits entrained fat particles to pass to scrubber unit 70. Condensate is returned by gravity to the reaction flask. The upward angle of tube 62 of tree 40 provides a rapid return of condensate.

The combination of the digestion temperature, the air flow provided by the working together of the vacuum pump and grooves 146, and the extent of condensation provided by a water-cooled condenser advantageously result in fat being blown out of the reaction vessel and into the scrubber unit. Otherwise, digestion of fat would increase the digestion time. Accordingly, the process provides for a selective separation of fat from digestate.

Uncondensed off gases and entrained fat particles are drawn by the vacuum pump via inlet tube 230 into the water trap in collector 96 of the scrubber unit. Off gases including moisture-laden sulfur dioxide, and entrained fat particles that escape the water trap, are then drawn into scrubber discs 238 of the scrubber tower. Discs 238 remove substantially all the sulfur dioxide and entrained fat particles.

Splash guard 246 prevents condensate on top of the uppermost scrubber disc from splashing over into line 252 and being drawn into filter 72. Any uncondensed sulfur dioxide is drawn by the vacuum pump into filter 72, which is preferably an activated carbon filter, and removed.

If desired, an activated carbon filter (not shown) may be located in the exit port of the vacuum pump. This filter would safeguard against the release of noxious fumes, such as sulfur dioxide fumes, into the ambient atmosphere.

After the dilution step is finished, the vacuum pump is turned off, and the scrubber tower is backflushed by pressurized air delivered from air pump 84, and a predetermined charge of hot water delivered through inlet 254. Solenoid valves 82,90 control the flow of pressurized air and hot water, respectively.

The backflush water is collected within collector 96. Backflushing cleans trapped off gases and fat from the scrubber discs, thereby regenerating the discs for further use.

During backflushing, solenoid valve 100 opens line 98 to drain the contents of the collector. Thereafter, solenoid valve 106 opens line 102 to rinse the collector, and solenoid valve 100 closes line 98 so that a predetermined volume of fill water is provided to the collector through line 102. The volume of water delivered, must be sufficient to immerse end 232 of inlet tube 230. The microwave system/scrubber system is now ready for another sample.

As can be understood from the foregoing description, the present invention provides as part of a microwave-based apparatus useful for digestion, a self-contained, scrubber system, which recharges itself. Only replacement of filter 72 is occasionally needed. Filter replacement is indicated by an indicator light (not shown).

Furthermore, it should be understood that the fluid delivery system for delivery of fluids to the reaction vessel through tree 40, and for the delivery of water to the condenser, may be provided as a portable, compact unit. Desirably, there is included in such a unit valve/-solenoid 106 for control of the fill water and valve/-solenoid 100 for control of collector drain line 98.

In FIG. 1, the self-contained, compact scrubber system is indicated by reference number 260, and the portable, compact fluid delivery system is indicated by reference numeral 262.

Advantageously, panels 120,122,124 provide for computer control of peristaltic pump 52, valves/-solenoids 58,82,90,100,106, and vacuum pump 66, and for information display. Accordingly, both the scrubber system and fluid delivery system are computer-regulated.

In the Example that follows and throughout this description and the claims set forth below, all percentages are by weight/weight, and all procedures are carried out at ambient temperature and pressure, unless otherwise specified.

EXAMPLE

A 1.0 g sample of meat is weighed out on a 24×40 microslide cover glass and dropped through a 29/42 ground glass joint of the neck of quartz, flat bottom, boiling flask 22 (500 ml). 11.5 ml of concentrated sulfuric acid, 0.75 g of mercuric oxide and 15 g of potassium sulfate are added to the flask.

Lower portion 130 of the flask is insulated by a molded, glass fiber cup 26 having a thickness of 4.5 mm+/1 mm. The insulated flask is placed on the platform in internal chamber 14 of microwave 12, flask mouth 136 is sealingly mated to ground glass surface 138 of ball joint 140 of the connector tube, and the microwave door is closed.

Equally distributed around the circumference of ball joint 140 are eight grooves 146. The area of a groove opening is 0.0015 sq.in. This area provides a flow rate per groove of 0.068 cfm, and a total flow rate of 0.544 cfm.

Under computer control, vacuum pump 66 is turned on and digestion is begun by the application of microwave energy to the flask contents. Under computer control, approximately 5 ml of a mixture of 1 part of concentrated sulfuric acid and 6 parts of 50% hydrogen peroxide, is rapidly added by peristaltic pump 52 to the reaction flask through inlet tube 190. At subsequent 30 second intervals, a second and a third 5 ml charge of the peroxide mixture are rapidly added.

Under computer control, two heating stages are used. A first heating stage with 100% power output lasts 1.5 minutes, and a second heating stage with 70% power output, last 2 minutes 40 seconds.

Immediately after the second heating stage, under computer control, there is a pulsed addition of water, followed by a continuous addition of water, to the reaction flask through inlet tube 190. For the first six pulses, the water input line is open for approximately 0.25 seconds and closed for approximately 3.75 seconds, and for the remaining pulses, the line is open for approximately 0.25 seconds and closed for approximately 1.75 seconds, with the pulsed addition lasting approximately 50 seconds. The water line is open thereafter for approximately 30–60 seconds.

During the digestion and dilution steps, the vacuum pump cooperates with grooves 146 to draw reaction off gases and entrained fat particles into water-cooled condenser 68. In the condenser, off gas condensate is formed. Condensate is returned by gravity to the reaction flask.

Uncondensed off gases and entrained fat particles are drawn by the vacuum pump into the water trap in collector 96. Off gases and entrained fat particles that escape the water trap, are then drawn into scrubber discs 238. Any uncondensed sulfur dioxide is drawn by the vacuum pump into activated carbon filter 72, and removed.

Under computer control, the vacuum pump is turned off, and the scrubber tower is backflushed by the delivery of pressurized air and a charge of hot water. Under computer control, the contents of collector 96 are drained, and the collector is charged with fill water.

The above example is illustrative of the present invention. It is to be understood that the example is not in any way to be interpreted as limiting the scope of the invention. Rather, it is intended that the scope of the invention be defined by the claims set forth below. It is contemplated that the invention as hereinafter claimed, will be subject to various modifications within the scope thereof.

Industrial Applicability

The microwave-based apparatus of the present invention is useful for rapid sample digestion, especially for macro-Kjeldahl digestions.

What is claimed:

1. Apparatus useful at operating temperatures of about 375°–425°C., comprising a microwave system comprising a chamber, microwave energy-generating means disposed exterior to said chamber, and means for transmitting microwave energy from said microwave energy-generating means into said chamber, wherein a wall forming said chamber has an aperture formed therethrough; a reaction vessel disposed within said chamber; a hollow tubular body that extends through said aperture into said chamber, and that has a generally spherical end sealingly joined to said reaction vessel, wherein a tapered, inner wall of the reaction vessel mouth is adapted to seat a portion of said generally spherical end such that a freeze-up preventing, tubular body to reaction vessel joint is formed; means for air flow into said hollow tubular body from said chamber; and external suction means connected to said hollow tubular body and in fluid communication with said means for air flow.

2. The apparatus of claim 1, further comprising biasing means for joining said hollow tubular body and said reaction vessel, said biasing means being located outside said chamber.

3. The apparatus of claim 2, wherein said biasing means is attached to said hollow tubular body and said wall.

4. The apparatus of claim 1, further comprising a microwave-transparent insulator, said insulator being within said chamber and surrounding said reaction vessel.

5. The apparatus of claim 1, wherein said means for air flow are grooves disposed in the sealed tubular body to reaction vessel joint.

6. The apparatus of claim 1, further comprising a tube for delivery of fluid into said reaction vessel, said tube being disposed within said hollow tubular body.

7. The apparatus of claim 6, wherein a side wall of a delivery end of the fluid delivery tube includes an opening.

8. The apparatus of claim 1, wherein said reaction vessel is made of quartz glass.

9. Apparatus comprising a microwave and scrubber system, said microwave system comprising chamber means and means for generating microwave energy, a reaction vessel being disposed within said chamber means; and a scrubber system comprising (a) suction means in fluid communication with said reaction vessel, and further comprising a conduit means disposed between, and providing for the fluid communication between, said reaction vessel and said suction means, said conduit means comprising the elements defined by (b), (c) and (d), as follows; (b) trap means for introducing off gas from said reaction vessel, into a column of water, (c) a residence reservoir for said off gas, containing said column of water, and (d) spaced apart from said column of water, a plurality of scrubber discs for removing noxious fumes from said off gas, said scrubber discs being spaced apart from one another and having pores for restricting flow of said off gas that escapes said column of water, such that off gas builds up and is contained within said residence reservoir.

10. The apparatus of claim 9, further comprising condensing means for condensing said off gas and for permitting particles entrained in uncondensed off gas to pass to said trap means.

11. The apparatus of claim 9, wherein said plurality of scrubber discs comprises a first scrubber disc having a relatively greater pore size than a second scrubber disc, and said second scrubber disc; said second scrubber disc being disposed between said first scrubber disc and said suction means.

12. The apparatus of claim 9, wherein a splash shield is disposed between said plurality of scrubber discs and said suction means.

13. The apparatus of claim 9, wherein said scrubber system further comprises means for backflushing said plurality of scrubber discs, said means for backflushing being in fluid communication with said plurality of scrubber discs.

14. The apparatus of claim 9, wherein said trap means comprises a container that serves as said residence reservoir.

* * * * *